United States Patent
Barrett

(10) Patent No.: US 10,281,454 B2
(45) Date of Patent: May 7, 2019

(54) TUNABLE OPTICAL RECEIVER

(71) Applicant: Fresenius Medical Care Holdings, Inc., Waltham, MA (US)

(72) Inventor: Louis L. Barrett, West Point, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 170 days.

(21) Appl. No.: 15/192,904

(22) Filed: Jun. 24, 2016

(65) Prior Publication Data

US 2016/0377530 A1    Dec. 29, 2016

Related U.S. Application Data

(60) Provisional application No. 62/183,792, filed on Jun. 24, 2015.

(51) Int. Cl.
*G01J 3/433* (2006.01)
*G01N 33/49* (2006.01)
(Continued)

(52) U.S. Cl.
CPC .......... *G01N 33/49* (2013.01); *A61M 1/14* (2013.01); *G01J 3/433* (2013.01); *G01N 21/31* (2013.01);
(Continued)

(58) Field of Classification Search
CPC ............ G01N 33/49; G01N 21/31; G01N 2021/3181; G01N 2201/0627; G01N 2201/12; G01J 3/433; H04B 10/66
See application file for complete search history.

(56) References Cited

U.S. PATENT DOCUMENTS 3,638,640 A    2/1972  Shaw
4,286,327 A    8/1981  Rosenthal et al.
(Continued)

FOREIGN PATENT DOCUMENTS

EP    2597454 A1    5/2013
JP    H09-264845 A    10/1997

OTHER PUBLICATIONS

International Search Report for co-pending International Application No. PCT/US2016/039419, dated Sep. 8, 2016.
(Continued)

*Primary Examiner* — Thanh Luu
(74) *Attorney, Agent, or Firm* — Leydig, Voit & Mayer, Ltd.

(57) ABSTRACT

An embodiment of the disclosure provides a system for determining information on one or more constituents in a medium. The system includes N light emitters $L_1 \ldots L_N$, wherein each light emitter $L_x$ provides an amplitude modulated (AM) light at modulation frequency $f_x$ into a flow path of the medium from one side of a containment vessel for the medium. The system further includes a photodetector, for receiving the AM light from each light emitter after it passes through the flow path of the medium, and converting the AM light to an electrical signal characterized by a summation of frequency components from each modulation frequency $f_x$. The system further includes one or more measuring circuits providing information about a concentration of one or more constituents in the medium determined from log ratios of a pair of amplitudes of $f_y$ and $f_z$ frequency components in the electrical signal.

16 Claims, 9 Drawing Sheets

(51) Int. Cl.
  *G01N 21/31* (2006.01)
  *A61M 1/14* (2006.01)
  *A61B 5/00* (2006.01)
  *A61B 5/026* (2006.01)
  *A61M 1/36* (2006.01)
  *A61B 5/145* (2006.01)
  *A61B 5/1455* (2006.01)

(52) U.S. Cl.
  CPC ........... *A61B 5/0059* (2013.01); *A61B 5/0084* (2013.01); *A61B 5/0261* (2013.01); *A61B 5/14542* (2013.01); *A61B 5/14551* (2013.01); *A61M 1/3627* (2013.01); *A61M 2205/3313* (2013.01); *A61M 2230/20* (2013.01); *A61M 2230/202* (2013.01); *A61M 2230/205* (2013.01); *A61M 2230/207* (2013.01); *G01N 2021/3181* (2013.01); *G01N 2201/0627* (2013.01); *G01N 2201/0691* (2013.01); *G01N 2201/12* (2013.01)

(56) References Cited

U.S. PATENT DOCUMENTS

| | | | |
|---|---|---|---|
| 4,596,043 A * | 6/1986 | Leitch | H03F 1/0266 332/159 |
| 4,800,885 A | 1/1989 | Johnson | |
| 4,848,901 A | 7/1989 | Hood, Jr. | |
| 5,061,632 A | 10/1991 | Shepherd et al. | |
| 5,218,207 A | 6/1993 | Rosenthal | |
| 5,404,021 A * | 4/1995 | Mangano | B23B 49/00 250/559.26 |
| 5,722,407 A | 3/1998 | Klingenbeck et al. | |
| 6,018,673 A * | 1/2000 | Chin | A61B 5/14552 356/41 |
| 6,117,099 A | 9/2000 | Steuer et al. | |
| 6,210,591 B1 | 4/2001 | Krivitski | |
| 6,563,585 B1 | 5/2003 | Rao et al. | |
| 6,725,072 B2 | 4/2004 | Steuer et al. | |
| 6,746,407 B2 | 6/2004 | Steuer et al. | |
| 8,518,247 B2 | 8/2013 | Akita et al. | |
| 9,212,988 B2 | 12/2015 | Akita et al. | |
| 2008/0208013 A1 * | 8/2008 | Zhang | A61B 5/0002 600/301 |
| 2010/0081897 A1 | 4/2010 | Li et al. | |
| 2012/0108928 A1 | 5/2012 | Tverskoy | |
| 2012/0120384 A1 | 5/2012 | Barrett et al. | |
| 2012/0154789 A1 * | 6/2012 | Barrett | A61B 5/14535 356/41 |
| 2013/0181613 A1 | 7/2013 | Schweninger | |
| 2016/0296687 A1 | 10/2016 | Scarpaci et al. | |

OTHER PUBLICATIONS

Hindle et al., *J. of Electronic Imaging*, 10 (3), 593-600 (2001).
European Patent Application No. 16 815 454.0, Search Report (dated Oct. 31, 2018).

* cited by examiner

| Approximate LED Wavelength | Blood Constituent | Modulation Frequency M(t) |
|---|---|---|
| 660nm | Oxygenated Hemoglobin (HbO2) | f1 |
| 590nm | Sodium + HbO2 | f2 |
| 750nm | Platelets + HbO2 | f3 |
| 800nm | Isobestic Hb | f4 |
| 790nm | COHb + HbO2 | f5 |
| 1300nm | H2O | f6 |

FIG. 3

TUNABLE OPTICAL RECEIVER

CROSS-REFERENCE TO RELATED APPLICATIONS

This patent application claims the benefit of U.S. Provisional Application No. 62/183,792, filed Jun. 24, 2015, which is incorporated by reference in its entirety.

BACKGROUND

Transmission of light through a medium, such as blood, consists of having a light emitter give off light, and the light then passes through the medium and is then incident on a photodetector. The emitter may be at least one light emitting diode (LEDs), laser, laser diode, or other device, and the photodetector could be a photodiode or other detection device.

An array of LEDs may serve as emitters and a matching photodiode may be used for detection. The term matching means that the photodetector has electrical characteristics such that the discrete wavelengths emitted by the array of LEDs produce a current in the photodetector. The range of wavelengths over which the photodetector can produce a current is termed the photodetector bandwidth. The photodetector currents can be amplified and converted to voltages through the use of a gain stage termed a Trans-impedance Amplifier (Trans-Z Amplifier).

SUMMARY

An embodiment of the disclosure provides a system for determining information on one or more constituents in a medium. The system includes N light emitters $L_1 \ldots L_N$, wherein each light emitter $L_x$ is configured to provide an amplitude modulated (AM) light at modulation frequency $f_x$ into a flow path of the medium from one side of a containment vessel for the medium, wherein each light emitter $L_x$ uses a different modulation frequency $f_x$, and wherein N is an integer greater than 1, and x is an integer greater than or equal to 1 and less than or equal to N. The system further includes a photodetector, configured to receive the AM light from each light emitter after it passes through the flow path of the medium, and convert the AM light to an electrical signal characterized by a summation of frequency components from each modulation frequency $f_x$. The system further includes one or more measuring circuits, configured to provide information about a concentration of one or more constituents in the medium determined from log ratios of a pair of amplitudes of $f_y$ and $f_z$ frequency components in the electrical signal, wherein y and z are integers greater than or equal to 1 and less than or equal to N, and y is not equal to z.

Another embodiment of the disclosure provides a method for determining information on one or more constituents in a medium. The method involves varying, by a driving circuit, current provided to N light emitters $L_1 \ldots L_N$ in a sinusoidal manner so that each light emitter $L_x$ provides an amplitude modulated (AM) light at modulation frequency $f_x$ into a flow path of the medium from one side of a containment vessel for the medium, wherein each light emitter $L_x$ uses a different modulation frequency $f_x$, and wherein N is an integer greater than 1, and x is an integer greater than or equal to 1 and less than or equal to N. The method further involves receiving, by a photodetector, the AM light from each light emitter after it passes through the flow path of the medium and converting the AM light to an electrical signal characterized by a summation of frequency components from each modulation frequency $f_x$. The method includes extracting, by a measuring circuit, log ratios of the amplitudes of $f_y$ and $f_z$ frequency components in the electrical signal to determine information about a concentration of one or more constituents in the medium, wherein y and z are integers greater than or equal to 1 and less than or equal to N, and y is not equal to z.

Yet another embodiment of the disclosure provides a non-transient computer readable medium containing program instructions for determining information on one or more constituents in a medium, such that when the instructions are executed by a processor coupled to N light emitters $L_1 \ldots L_N$ and a photodetector, the processor performs a method. The method performed by the processor includes varying driving current provided to the N light emitters in a sinusoidal manner so that each light emitter $L_x$ provides an amplitude modulated (AM) light at modulation frequency $f_x$ into a flow path of the medium from one side of a containment vessel for the medium, wherein each light emitter $L_x$ uses a different modulation frequency $f_x$, and wherein N is an integer greater than 1, and x is an integer greater than or equal to 1 and less than or equal to N. The method performed by the processor further includes extracting log ratios of amplitudes of $f_y$ and $f_z$ frequency components in an electrical signal to determine information about a concentration of one or more constituents in the medium, wherein y and z are integers greater than or equal to 1 and less than or equal to N, and y is not equal to z. The electrical signal is generated by a photodetector receiving the AM light from each light emitter after it passes through the flow path of the medium and converting the AM light to an electrical signal characterized by a summation of frequency components from each modulation frequency $f_x$.

BRIEF DESCRIPTION OF THE SEVERAL VIEWS OF THE DRAWINGS

The present invention will be described in even greater detail below based on the exemplary figures and embodiments. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 3 provides an example of how wavelengths may be "tagged" with a modulation frequency to distinguish light intensities affected by different blood constituents;

DETAILED DESCRIPTION

The emitter-photodiode system described in the Background section has some inherent drawbacks, mostly linked to the limitations of photodiodes in the real world. For example, photodiode bandwidth may reduce overall response of the system rendering some emitter-photodiode systems useless. To overcome the inherent limitations, embodiments of the disclosure treat the emitter-photodiode system in a similar manner as a communications technology system.

Communications technology uses various techniques, in particular, the concepts applicable to different methods of amplitude modulation (AM) and demodulation. These concepts are applied in various instances, for example, AM radio and AM broadcasting. There is an inherent improvement in the use of synchronous detection compared to the use of modulation envelope detection. Utilizing techniques in communications technology, the emitter-photodiode system may be improved upon.

Figure 1:
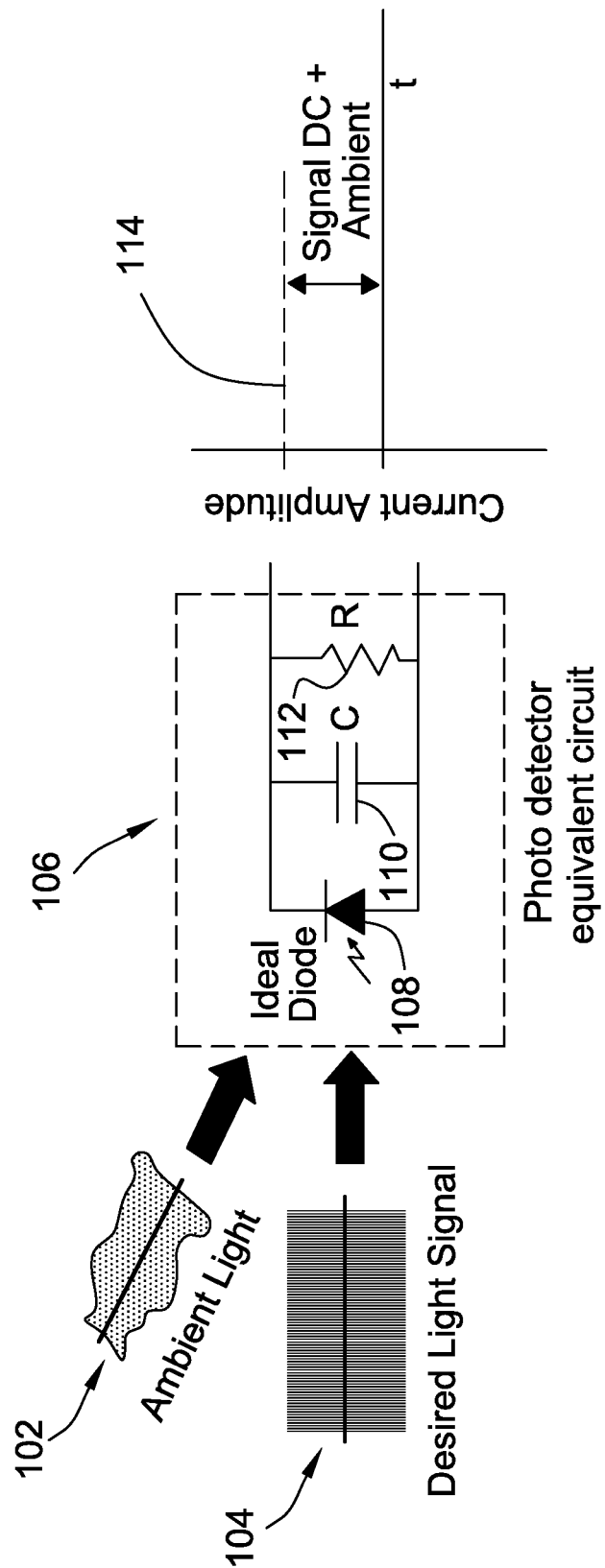
FIG. 1 is a sample illustration of a photodetector's source inputs and electrical outputs.

A model of a commonly realizable photodetector 106 is shown in FIG. 1. As provided, only the output terminals of the model can be accessed in the real world as shown in this "black box" model. FIG. 1 also provides the dynamics of the photodiode photodetector 106. Diodes are made by fusing dissimilar semi-conductor materials (such as Silicon) which are "doped" with chemicals to create the sensitivity to a bandwidth of light wavelengths. In a diode, electrical current only flows in one direction on each cycle of the frequency of the impressed light. Internal to the black box is a theoretical or ideal photodiode 108 which has no limitations to current production or speed within its bandwidth.

In the ideal photodiode 108, any wavelength in its bandwidth will generate a half wave rectified current when the diode is forward biased by the impressed light signal from a light emitter. The frequency of the current matches that of the light. Frequency is determined in this case by dividing the speed of light (approximately $3 \times 10^8$ meters/second) by the wavelength in meters. The resulting frequencies in the near infrared and visible light spectrum measure in the terahertz range.

In some situations, the photodiode photodetector 106 receives various light input from ambient sources identified as ambient light 102 and a desired light signal 104 from a light emitter. The light signal is impressed on the junction of the photodiode and the internal junction capacitance along with leakage of the semi-conductor material result in a lowpass filter. The light signal is alternating current in the terahertz frequency range (with cycles so close together in time that the light signal is shown as a continuous block). By modeling an ideal photodiode photodetector with the equivalent circuit as shown in FIG. 1, depending on the values of the resistor and capacitor models, the equivalent circuit is unable to respond to the terahertz frequency thus resulting in the output of the photodiode photodetector 106 being a rectified and filtered Direct Current (DC) signal with amplitude proportional to the amplitude of the impressed light signal (i.e., the combination of the ambient light 102 and the desired light signal 104).

As discussed, in the real world realization of a photodiode photodetector, the "ideal" characteristics are spoiled by the capacitance of the internal junction "space charge layer" and small leakage currents in the semiconductor material. In the black box model shown, these are represented by a discrete capacitor 110 (collective of all internal capacitances) and a discrete resistor 112 (collective of all leakages), respectively. This resistor-capacitor (RC) network forms a "lowpass filter" which filters the extremely high frequency components of the light impressed and detected by the ideal diode 108. Due to this lowpass filtering of the detected current, rather than a half wave rectified representation of the light waveform appearing at the black box terminals, a current proportional to the intensity of the impressed light without frequency appears—in other words a DC current.

If the Alternating Current (AC) frequency component of the impressed light could be preserved in the photodiode photodetector and components capable of operating at these frequencies were available, then there would be a way to distinguish the wavelength of the received light illuminating the photodetector. But with only DC current being produced for all light impressed on the photodetector within its bandwidth, there is no ability to distinguish what individual wavelengths are being received. The photodetector simply integrates all of the light energy received in its bandwidth and produces a composite DC current as a result. This would not be a problem if ambient light sources could be eliminated in all situations.

Unfortunately, in the real world all light sources are not well controlled. Light sources such as overhead lighting, reflections, panel lights, windows, etc., can invade a light wave based system. Under these conditions, it is impossible to determine from the photodiode photodetector what light sources are creating its output current. From FIG. 1, the intensity of the desired wavelength is sought after and is intended to be measured. However, with the contributions from undesired "ambient light" 102, the DC current of the photodiode photodetector includes an unquantifiable amount of "ambient light."

In attempts to distinguish the desired wavelength of light being detected from interfering ambient light, a common method used and commercialized are so called "Lock-in" amplifiers. In such systems the desired light beam is either physically chopped by a rotating disk with holes in it or by electronic means which, in effect, keys the light on and off at a specified rate. The photodetector amplification circuitry is synchronized to the light chopping so it only processes signals when the desired light is known to be emitting. During the period of no light emission, the background level of ambient light is measured and subtracted from the time when active light is known to be emitting. This difference is considered to be the desired signal amplitude.

However, the limitation to this approach is that often the amplitude of the true light signal is very small compared to elements of the ambient interference such as overhead lighting. Overhead lighting often is very invasive and contains a modulation related to the power line frequencies. Under these circumstances, the sampling rate of the chopped light must be at a high enough frequency that the background measurement is not "aliased" by the frequency of the ambient interference. Small signal measurements under these circumstances are very difficult and often not reliable.

A more effective method is the application of communications amplitude modulation techniques. This approach is based on the realization that while the lowpass filter characteristic of the photodetector will not preserve the frequency of the light, the light can be AM modulated with a frequency that is low enough that the photodetector acts as a conventional envelope detector as found in traditional AM receivers. In this case, instead of the carrier being in the radio frequency (RF) spectral region, the carrier is the light determined by the emitter's wavelength. In AM, the tone modulation amplitude at a fixed modulation index is proportional to the strength of the carrier—therefore, the strength of the light signal. Therefore, processing the modulation sideband allows for distinguishing the wavelength of interest over ambient interference.

The concept of the system described herein is to view the bandwidth of the photodetector as a segment of RF spectrum. This is possible because it is generally agreed that light is an electro-magnetic energy which behaves very much like RF.

Figure 2:
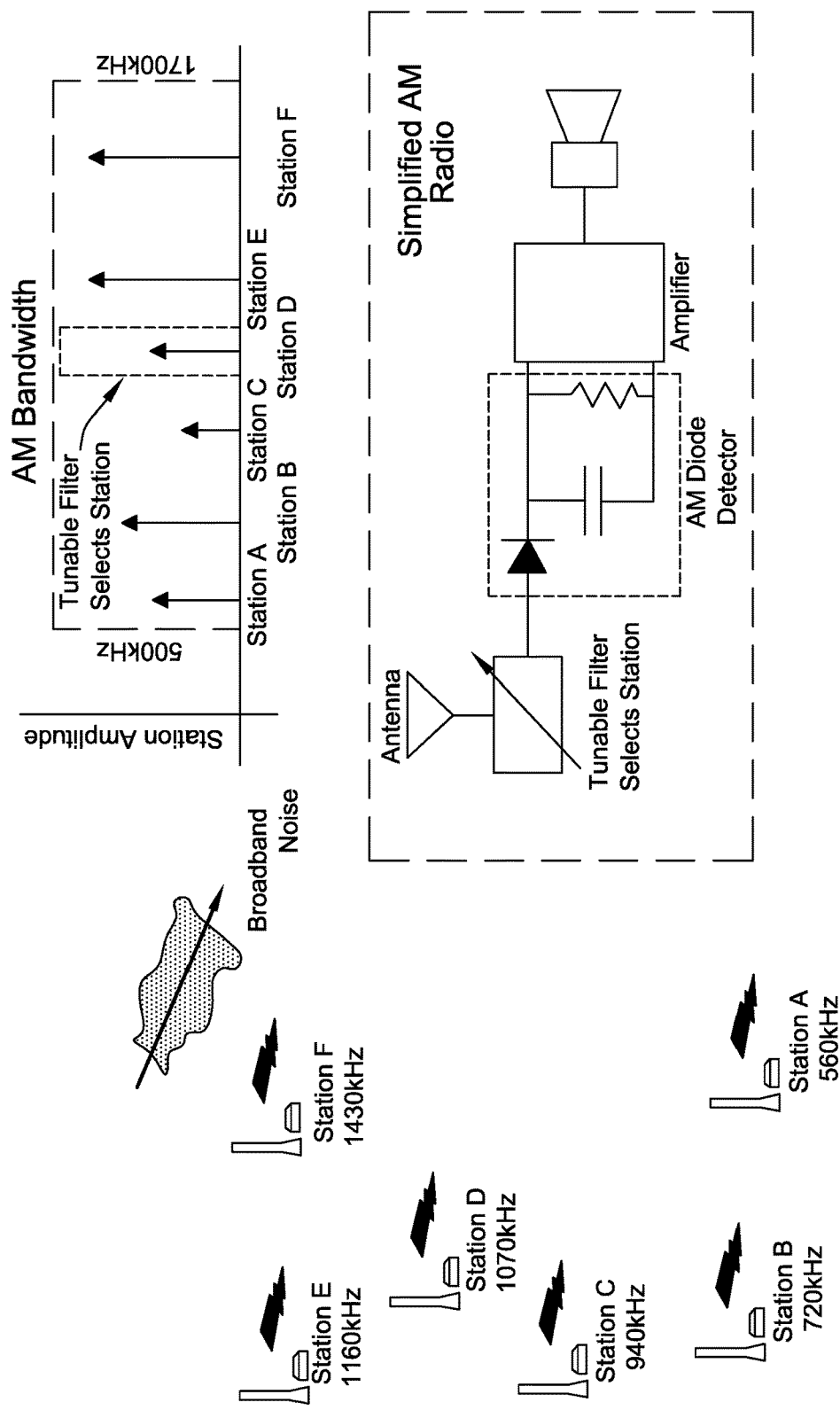
FIG. 2 illustrates the operation of a sample AM radio.

To illustrate the concept of the system described herein, consider the standard AM broadcast bandwidth in the United States covers RF signals on frequencies from 500 kHz to 1700 kHz as provided in FIG. 2. An AM receiver is built to tune any of the frequencies (or wavelengths where wavelength is the speed of light—$3 \times 10^8$ meters/second—divided by the frequency). The conventional diode detector in an AM receiver generates asynchronous envelope detection—the same as the previously described light photodetector—but in the envisioned system the frequency of the RF carrier is low enough that circuit provisions are made to add a physical lowpass filter. The lowpass filter is made up of an appropriate capacitor and resistor that are tuned to eliminate all frequencies above the music audio frequency range. The simplified AM radio in FIG. 2 shows that the antenna receives all transmitted frequencies, the tunable filter selects a frequency of interest, and in this case, Station D, and the AM diode detector functions as an envelope detector and a lowpass filter based on the appropriate capacitor and resistor combination. The signal from the AM diode detector is provided in an Amplifier which then goes to the speaker for audio out.

If the AM detector diode circuit was connected directly to the antenna, all AM broadcast signals in the entire AM bandwidth—regardless of assigned frequency within that spectrum—would be heard, and the programming audio of each station would be additive and overlap each other. (In addition, all noise in the bandwidth would be included in the detection.) It would be impossible to distinguish a single station—the strongest one would be dominant—but all would be heard.

This confusing situation is much like the situation with a photodetector when multiple competing direct light signals and/or ambient light sources are impressed on the photodetector while trying to detect a single, specific light signal.

To solve this problem in the AM radio, each receiver contains a set of selective tuning circuits, between the antenna and the AM diode detector as provided in FIG. 2, used to "pre-select" the signal to be received. The bandwidth of the tuning circuits is narrow enough (sufficiently high enough Quality factor—or "Q") to eliminate all but the specific radio station one desires to listen to. One tunes these selective tuning filters with the tuning knob on the radio to pick a preferred station for detection. Only the RF from that specific station passes to the detector and the programming is stripped off by the detector and RC lowpass filter to be amplified to the speaker. FIG. 2 illustrates the AM radio concept and spectrum.

According to the system described herein, a tunable optical receiver is provided in connection with a light measurement system that enables control over the transmission systems of the light signals. The described system enables selection of wavelengths in the photodetector bandwidth that are conveniently absorbed and scattered by specific constituents in the medium being measured. Unique modulation frequencies are assigned to each of the transmitted wavelengths. Each of the modulation frequencies and its corresponding transmitted wavelengths are selected to be non-harmonically related, and thus will act as "tags" for the respective light signals. In various embodiments and aspects, the tunable optical receiver may be configured to use asynchronous and/or synchronous detection of the modulation tags. The application of this tunable technology can form the basis of a bedside diagnostic suite for future clinical treatments. Two example embodiments will be provided herein to describe a system and method of dealing with ambient light. One embodiment applies to an asynchronous receiver and the second embodiment to a synchronous receiver.

Asynchronous Receiver Embodiment

In applying the AM signal selection principles to light, the approach is similar to AM transmission principles discussed but with modified electronic signal processing techniques. Unlike in the case of the AM receiver, there are no currently available components that will function in visible light frequency range to "pre-select" a particular light signal to receive and measure. Therefore, the electronic components to build a tunable filter with a high Q in the optical frequency range are unavailable. As such, in the circuit architecture of the AM receiver of FIG. 2 when applied to optical frequencies, the photodetector will receive all generated and ambient light simultaneously and demodulate them. Thus, the output electrical form is the sum of all signal contributions including any undesired light signals.

In conventional light measurement systems, the light is either continuous wave (on all the time—CW) or keyed on and off (On-Off Keying—OOK) as in the Lock-in Amplifier schemes. The absorption and scattering of the light through the medium to be measured reduces the signal where the photodetector quantifies it for processing using Beer's Law. Using the AM radio analogy, this is like a radio station either turning on the transmitter in CW mode or toggling the transmitter on and off in OOK mode, but never playing any programming material (music, talk, etc.)—what is termed in the broadcast industry as "dead air."

In the AM radio receiver example, there is no control over the status or operation of the transmitter system. However, in a light measurement system there is total control over the transmission of the light signals. There are three key points to the system described herein:

(1) The designer has total control over the transmission systems of the light.

(2) The designer can select wavelengths in the photodetector bandwidth that are conveniently absorbed and scattered by specific constituents in the medium being measured.

(3) The designer can assign a unique modulation frequency, $M(t)_n$ to each of the transmitted n wavelengths to act as "tags" for the respective light signals defined in point #2. The modulation frequencies are chosen so that they do not have a harmonic relation with each other and separated sufficiently to be individually filtered by conventional filtering techniques (analog, active filter, digital, etc.).

As an example, consider a system built to measure certain parameters where light is used in discrete spectroscopy to analyze human blood. FIG. 3 suggests some possible wavelengths for those parameters. The designer then selects frequencies of M(t) to "tag" each wavelength strategically for independent detection in the receiver. In FIG. 3, wavelengths can be "tagged" with a modulation frequency M(t) to distinguish light intensities affected by different blood constituents. This approach removes ambient light interference, quantifies, and offers significant signal to noise margins for otherwise difficult to measure components of Human blood. This approach can be used equally well in other applications outside of blood such as monitoring purity of hydraulic fluid in aircraft.

In the example of FIG. 3, note that each wavelength of light is individually chosen to measure Oxygenated Hemoglobin (~660 nm), Sodium (~590 nm), Platelets (~750 nm), Isosbestic Hemoglobin (~800 nm), Carboxi-Hemoglobin (~790 nm) and Water (~1300 nm). The AM modulation "frequency tags" are shown as well in FIG. 3 (f1 to f6, which are not harmonically related and separated sufficiently to be individually filtered by conventional filtering techniques (analog, active filter, digital, etc.)).

There are multiple ways to tag light coming from an emitter. For example, when using LEDs as emitters, a current source may be used to drive the LED. In an LED device, the photon yield is directly proportional to the current flowing through the device. Photon yield is directly related to the light intensity. Given an LED that emits light at a specific wavelength (for example, one of the wavelengths provided in FIG. 3) the higher the photon yield, the higher the light intensity. The current source driving the LED may be programmed to change current delivered to the LED in a specified fashion, for example, in a sinusoidal fashion with a frequency matching one of the modulation frequencies M(t) provided in FIG. 3. By doing so, the LED's light intensity (photon yield) will vary to a maximum with current in the positive cycle and then to nearly zero (or zero) in the negative cycle. As such, a "tagged" light is realized thus the light emitted by the LED is AM modulated with modulation frequency M(t). An example waveform showing a desired "tagged" light 404 is provided in FIG. 4. M(t) is preferred to be sinusoidal.

M(t) may be a frequency in the range of 100 Hz to 500 kHz. The 100 Hz lower end is limited by the size of coupling capacitors, since the size of coupling capacitors increases as frequency decreases. Common optical systems are based on DC and need to be compensated for temperature drifts, input biases to amplifiers, and DC offsets, etc. By operating an AC system, some of the problems with a DC system are alleviated. By choosing an acceptable 100 Hz frequency in the AC system, acceptable sizes of a coupling capacitors may be realized. The 500 kHz upper end on M(t) is limited by electromagnetic (EM) radiation. At RF frequencies or frequencies above 500 kHz, EM radiation should be taken into account. Some jurisdictions have radiation emission standards to limit RF emissions in medical devices, for example, the International Electrotechnical Commission IEC 60601 standard.

Figure 4:
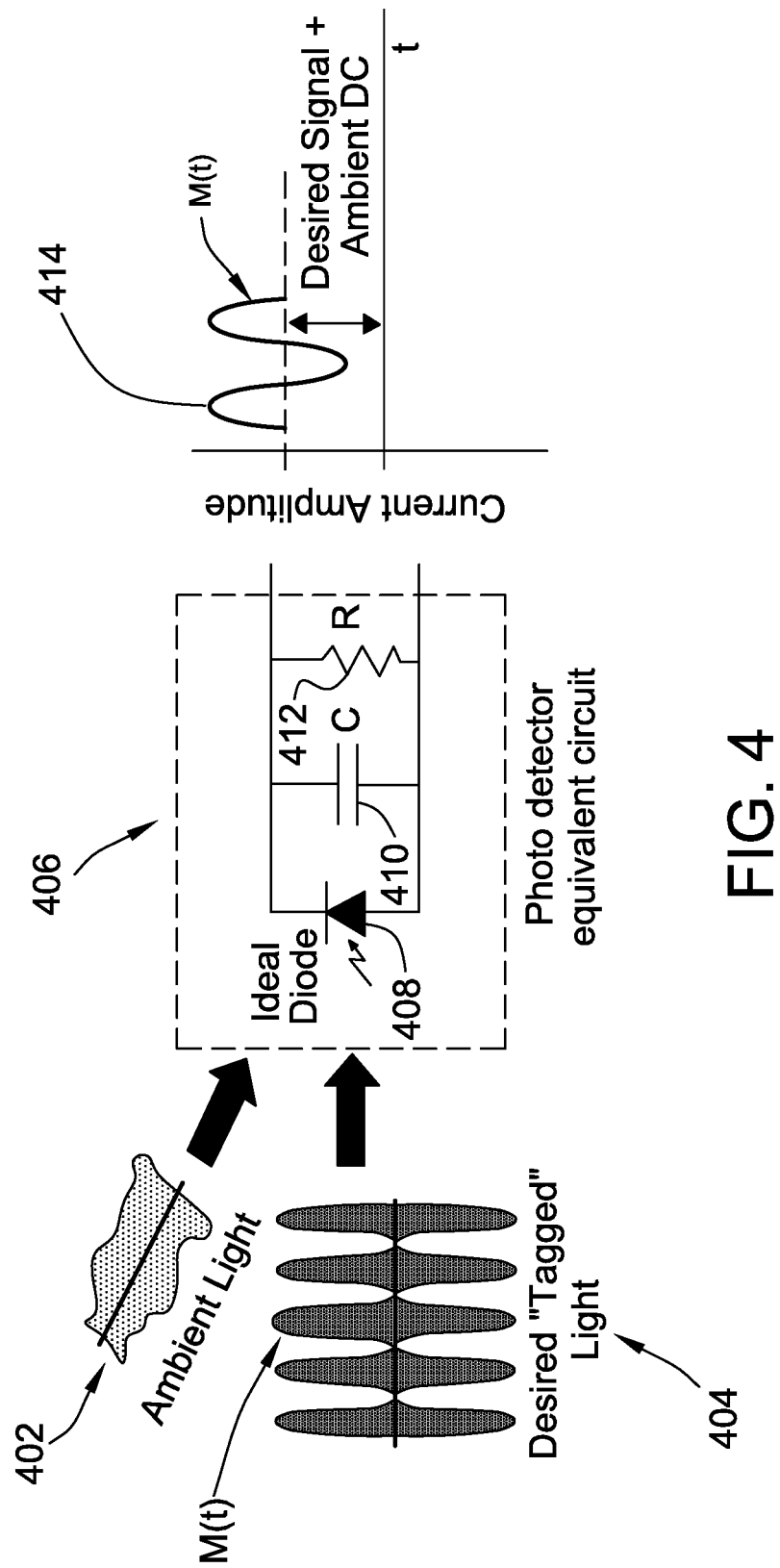
FIG. 4 illustrates a sample electrical output when using a photodetector to detect "tagged" light.

While true that the photodetector cannot "pre-select" what light signals within its bandwidth it can receive for detection, it is also true that the modulations from each light signal will be summed in the output current of the photodetector. As shown in FIG. 4, the photodetector 406 output current sums the DC levels from the received signals with any and all ambient interference—plus the modulation tones. Ambient light 402 and desired light 404 produce a sinusoidal signal 414. Because ambient light 402 is not modulated, it shows up as a DC component and adds with the DC component of signal 404 at item 414 with M(t) of the desired light offset by the total DC signal at 414. All are then amplified and converted to voltages through a Trans-Z amplifier.

Figure 5A:
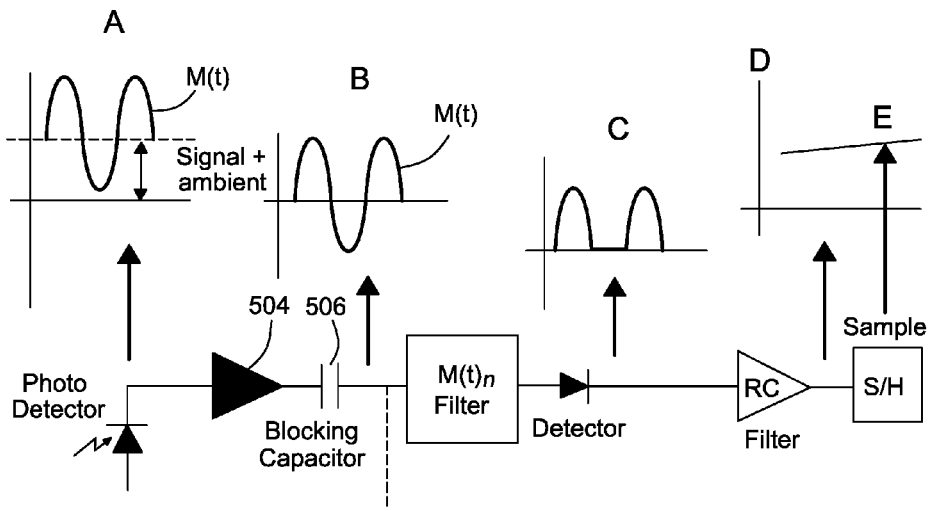
FIG. 5A-B illustrate receiver architectures for an asynchronous receiver according to various embodiments of the disclosure.
Figure 5B:
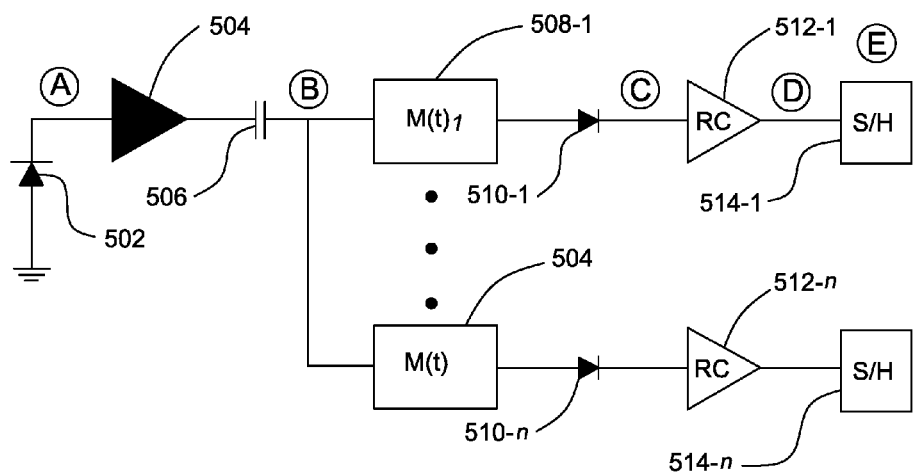

Referring to FIGS. 5A-B, by passing the signal from the Trans-Z amplifier 504 through a coupling capacitor 506, the DC component is removed (including all interfering and ambient light) leaving only the modulation frequencies of the individual "tagged" signals of interest. This is key to the removal of all interfering ambient light signals in the environment the measurements are made in.

At this point, each frequency can be independently filtered and asynchronously envelope-detected with an additional detector for each tag frequency. FIG. 5A-B shows this type of arrangement of the receiver where individual filters 508-1 through 508-$n$ may be bandpass filters that select the lower modulation frequency of the different desired signals. In some cases if only one modulation frequency is used, then only one path exists as in FIG. 5A. The 510-1 through 510-$n$ diodes are detectors that rectify the signal from the 508-1 through 508-$n$ filters. Using lowpass RC filters 512-1 through 512-$n$, the rectified signals are smoothed out. This smoothed DC level is proportional to the light amplitude at the respective tagged wavelength. In some embodiments, sample and hold circuits 514-1 through 514-$n$ are provided to select a single sampled voltage value on the smoothed signals for interface to digital processing systems.

FIG. 5A shows a simple case when only one tagged signal is detected. The different graphs are shown as example representations of what the signal may look like in time as it propagates through the stages of the receiver. After the photodetector, at point A, a preferred sinusoidal signal M(t) with a DC offset is received (as in FIG. 4). After the blocking capacitor or coupling capacitor, the DC signal is removed thereby giving the graph depicted at point B. The DC signal removal signifies removal of the ambient signal. After the detector, the rectified signal is provided at point C. The detector in this case operates as a half-wave rectifier, but it is understood that a diode bridge circuit or other circuit may be used to full-wave rectify the signal from point B. After RC filtering, the smoothed graph is provided at point D. The DC voltage at point D is proportional to the intensity of the selected (filtered) received light signal. The sample and hold circuit then selects a measured value at point E. FIG. 5B shows that the photodetector 502 may receive multiple tagged light with undesired light signals and the intensity of each of the desired signals may be quantified as a voltage in parallel using a similar process shown in FIG. 5A. In FIG. 5B, multiple outputs would be read in parallel from each of the sample and hold circuits 514-1 through 514-$n$. In FIG. 5, every component coming after blocking capacitor 506 may be generally referred to as being part of a measuring circuit since the collective effort is to measure the amplitude of the signal at point B.

The underlying math for this asynchronous approach is based on the fundamental AM equation 1:

$$E = A(1 + B(M(t))\mathrm{Cos}\,\Omega_L t \tag{1}$$

where E is the overall wave amplitude at any given time, A is the maximum voltage of the AM waveform, and B is the modulation index (a value from 0-1). In this optical system, B is always 1. M(t) is the modulation frequency function which may be defined as $\mathrm{Cos}\,\Omega_M t$, with $\Omega_M$ being the frequency of modulation measured in radians/second. $\Omega_L$ is the frequency of the light signal measured in radians/second, and t is the time the snapshot of that this waveform is taken for analysis.

Expanding equation 1 with B=1 and trigonometry identities provides equation 2:

$$E = A\mathrm{Cos}\,\omega_L t + \frac{A}{2}\cos(\omega_L \pm \omega_M)t \tag{2}$$

When this overall wave amplitude E is applied to the photodetector, the device cannot respond to the light frequency due to the internal lowpass filtering of the space charge layer capacitance and the material leakage. The result is a DC current output in place of the light frequency. Though there will be some loss in the system, the output value will still be a proportional amount of A. For this discussion, assume the system to be lossless for ease of explanation. Revising equation 2 with the light frequency terms now DC ($\Omega_L=0$) provides equation 3:

$$E = A + \frac{A}{2}\cos \omega_M t \quad (3)$$

The DC offset is the first A term. The second term is simply the modulation term of frequency $\Omega_M$. The negative of the modulation frequency per equation 2 is not realizable due to physical constraints of the real world.

As shown in FIG. 5A, passing the signal through a series capacitor removes the DC term (point B of FIG. 5A) from equation 3. The signal is then reduced to equation 4:

$$E = \frac{A}{2}\cos \omega_M t \quad (4)$$

It follows that if there are additional light sources with differing modulation frequencies for $\Omega_M$ (i.e. $\Omega_{M1}$, $\Omega_{M2}$, $\Omega_{M3}$ ... $\Omega_{Mn}$), then after the photodetector detection and passing through the series capacitor, only the vector sums of these frequencies would remain in the signal for detection. Each of these signals will be proportional in amplitude to the respective original light intensity, A from equation 4 at each wavelength. That is, the amplitude of $\Omega_{M1}$ will be proportional to $A_1$, the amplitude of $\Omega_{M2}$ will be proportional to $A_2$, etc.

As shown in FIG. 5B, for each anticipated constituent frequency, M(t), an asynchronous detector will require a separate bandpass filter to select the M(t) from the composite detected modulation at the output of the Trans-Z amplifier 504 and series capacitor 506. The selection of M(t) frequencies must be such that there is no harmonic relationships that will excite the incorrect filter, and that the M(t) frequencies are separated enough in frequency that the Q of the bandpass filters are reasonable and realizable. This is the complexity and design constraints on the realization of this embodiment of the tunable optical receiver.

Synchronous Receiver Embodiment

In a second embodiment, another method to receive the light signals is to synchronously detect using the original modulation frequency from the transmitter side as the base injection frequency. The synchronous detection is advantageous compared to the asynchronous due to lower component count and less rigor in design of selective filters 508 of FIG. 5B.

Further, synchronous detection also provides for potential differential phase measurement of the received modulation phase compared to that transmitted through the medium under test. There may be important information included in these phase differences, for example, the ability to use the same signal to sense two components or properties—one component sensed through the signal's amplitude and the other component through the signal's phase. Phase differences between an input light signal and an output light signal occur when the wave velocity slows down as the wave travels from one medium to another. In the synchronous case, the phase of the initial signal is known, and the phase of the received signal can be measured. The difference in phase between the two signals may be calculated.

For example, when looking through an artery, the difference in phase between the input signal and the obtained signal may average about $\varphi_1$ degrees. When a microclot (much denser than blood) moves through the artery, this may affect the light velocity propagated through the artery. This may show up as a $\Delta\varphi$ degree change in phase to detect the microclot as it passes. As such, the phase shift from $\varphi_1$ degrees to $\varphi_1+\Delta\varphi$ degrees can be seen and the signal may be used to identify that a microclot just passed through the artery. Different bodies may produce different phase shifts, therefore, phase of a signal provides an additional dimension to recognize bodies in a medium while sensing for a constituent of the medium with the amplitude of the signal.

Figure 6:
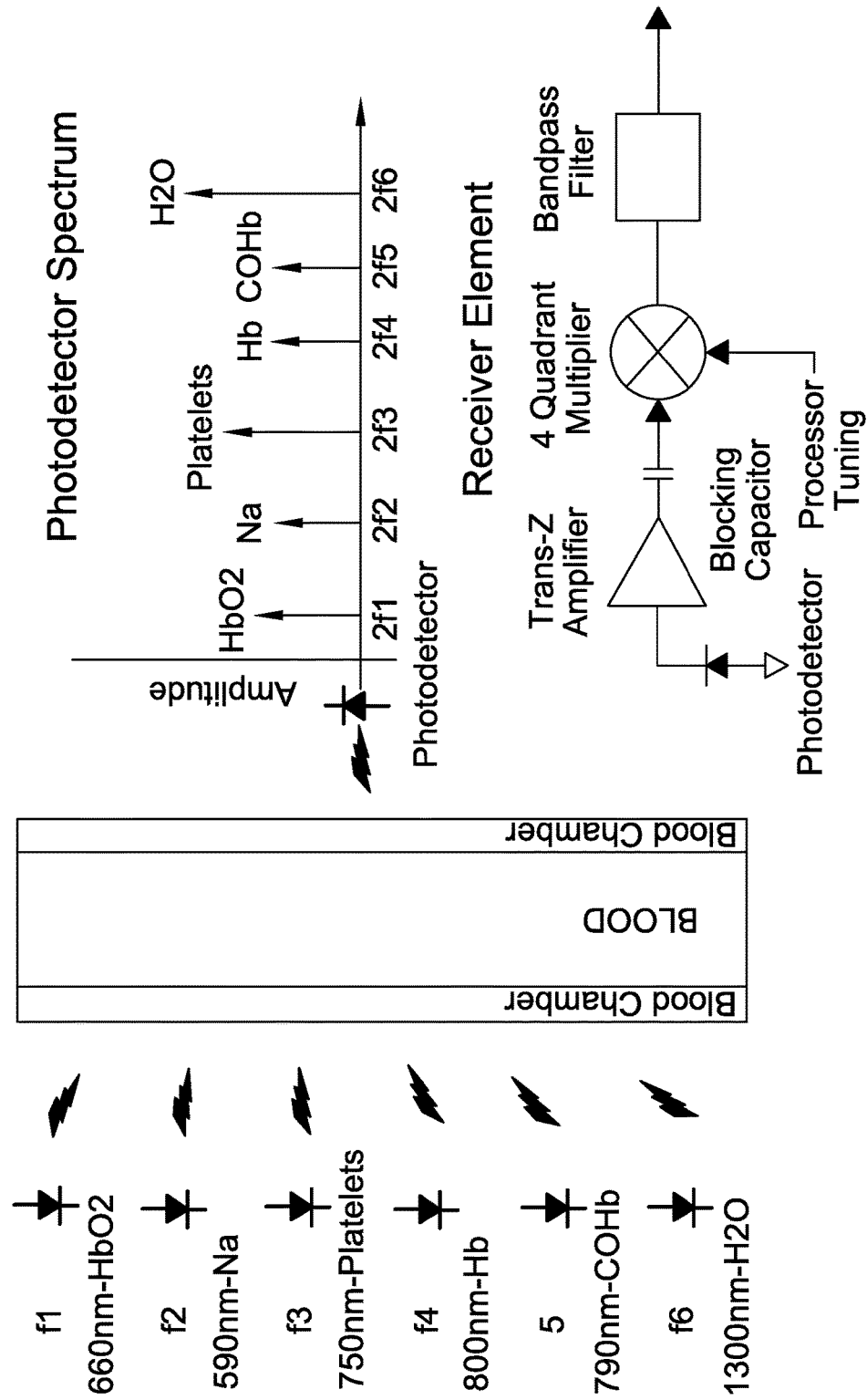
FIG. 6 illustrates a synchronous receiver architecture for determining blood constituents in accordance with various embodiments of the disclosure.

FIG. 6 illustrates one embodiment of the tunable optical receiver which uses synchronous detection of the modulation tags. This system represents an example where a number of measurements through a blood chamber filled with human blood are made. Based on the governing mathematics below, it can be shown that as the processor tuning frequency is changed in each receiver element to correspond to a "tag" frequency, an independent measurement of the medium can be made.

Consider equation 4 where multiple modulation frequencies, $\Omega_{Mn}$, have been detected by the photodetector, amplified by the Trans-Z amplifier, and then stripped of the DC components by the series capacitor following the Trans-Z amplifier. Equation 5 describes the signal following the Trans-Z amplifier as:

$$E = \quad (5)$$
$$\frac{A_{M1}}{2}\cos \omega_{M1}t + \frac{A_{M2}}{2}\cos \omega_{M2}t + \frac{A_{M3}}{2}\cos \omega_{M3}t + \ldots \frac{A_{Mn}}{2}\cos \omega_{Mn}t$$

In the asynchronous case, it is necessary to build a bandpass filter for each $\Omega_M$ followed by an additional independent detector, filter and voltage measurement circuit. However, in using a synchronous detector according to some embodiments of the disclosure, such as the receiver element shown in FIG. 6, there are two ways of recovering the amplitude, $A_{Mn}$, of any given light source. Both involve the use of a four quadrant multiplier realized in circuitry either by a dedicated device or through the use of software based in a micro-controller, digital signal processor or other computing device. This allows for any receiver element to be "tuned" to any of the light sources available from the Trans-Z amplifier as mathematically described in equation 5.

For example, suppose $A_{M3}$ is of interest for a given interval of time. To receive this signal specifically, the processor tuning line to the four quadrant multiplier is set by the processor to $\Omega_{M3}$. Using equation 5 as an example, after removing the DC component, the signal is multiplied with a signal C cos $\Omega_{M3}t$ to obtain equation 6:

$$D = C\cos \omega_{M3}t\left[\frac{A_{M1}}{2}\cos \omega_{M1}t + \right. \quad (6)$$

-continued
$$\frac{A_{M2}}{2}\cos\omega_{M2}t + \frac{A_{M3}}{2}\cos\omega_3 t + \ldots \frac{A_{Mn}}{2}\cos\omega_{Mn}t]$$

where D signifies the detected signals, $A_M$ is the amplitude of each of the individual light signals, C is the amplitude of the processor injection signal (a constant), $\cos\Omega_{Mn}t$ is the light wave tags detected out of the Trans-Z Amplifier, $\Omega_{Mn}$ is the radian frequency of the modulation tags measured in radians/second, and t is the time the snapshot of this waveform is taken for analysis.

Expanding equation 6 provides equation 7:

$$D = \frac{CA_{M1}}{4}\cos(\omega_{M1}\pm\omega_{M3})t + \frac{CA_{M2}}{4}\cos(\omega_{M2}\mp\omega_{M3})t + \quad (7)$$
$$\frac{CA_{M3}}{4}\cos(\omega_{M3}\pm\omega_{M3})t + \ldots \frac{CA_{Mn}}{4}\cos(\omega_{Mn}\pm\omega_{M3})t$$

Note that the action of multiplying the "tag" signals by the processor tuning frequency tends to "spread" the resulting frequencies emerging from the four quadrant multiplier. This aids in filtering the desired amplitude for measurement.

Referring to the third term in equation 7, there are two ways to filter the $\Omega_{M3}$ component. The first is to follow the four quadrant multiplier with a bandpass filter tuned to $2\Omega_{M3}$, as provided in FIG. 7B, followed by a root mean square (RMS) voltmeter, a diode/RC filter circuit with a sample and hold, as in FIG. 5, or other measurement circuit. The bandpass filter will reject all the rest of the frequency terms from the four quadrant multiplier. The second way is use a lowpass filter to measure the DC offset of the output of the four quadrant multiplier—which is the amplitude of $(\Omega_{M3}-\Omega_{M3})$. All of the rest of the frequency terms from the Four Quadrant Multiplier are rejected by the lowpass filter. Since the second way is measuring a DC signal, it is important that a blocking capacitor is used after the Trans-Z Amplifier as in FIGS. 7A and 7B to eliminate any possible DC feedthrough from the Trans-Z Amplifier circuit.

In yet another embodiment of the synchronous receiver, another option in detection is to shift the processor tuning frequency by a fixed offset—such as 200 Hz—from the desired tag frequency $\Omega_{M3}$. In this case, a lowpass filter will yield a 200 Hz signal proportional to the amplitude of the light signal. In some instances, this signal may be easier to measure than a DC signal. It is also of note to see that the amplitude of the signal provided by the processor tuning frequency, C, applies a gain factor to the overall detection process.

FIG. 6 shows a system, based on some embodiments of the disclosure, using synchronous detection where the receiver element(s) are under processor tuning control. The figure uses the option of filtering twice the tag frequency, taking advantage of the spectrum spreading as a result—thus simplifying the filter designs. In some instances, this system is advantageous in situations that exhibit steady state transmission of the light sources simultaneously (not pulsed).

Figure 7A:
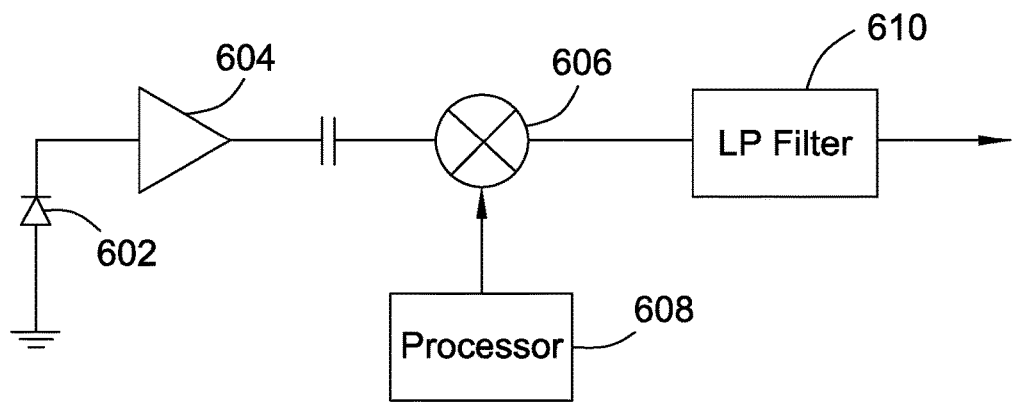
FIGS. 7A-B illustrate various embodiments of synchronous receiver architectures.
Figure 7B:
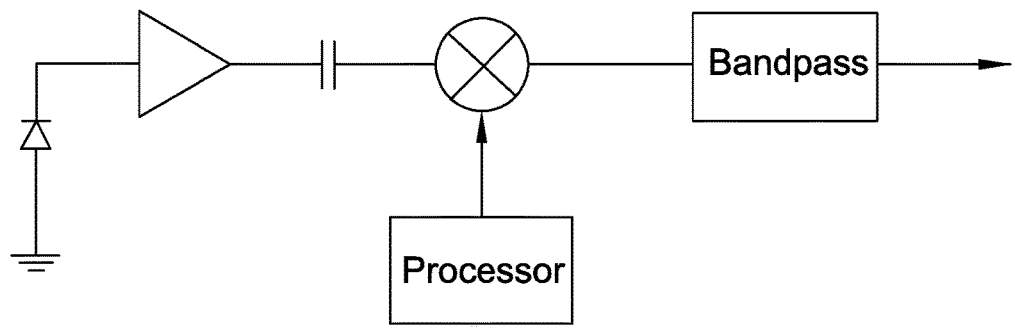

FIGS. 7A and 7B illustrate some embodiments of the synchronous receiver architecture. In FIG. 7A, item 610 may be a lowpass filter or a bandpass filter for some offset frequency. This architecture may be used when sensing a DC offset as the amplitude corresponding to the selected frequency component. This architecture may also be used when sensing a low frequency signal at some offset frequency, for example, 200 Hz. The amplitude of the offset frequency signal, in this case, corresponds to the output of the selected frequency component. FIG. 7B is provided separately to show the architecture where a bandpass filter may be used to select a signal that has a frequency twice the selected component's frequency. This approach takes advantage of frequency spreading, so the amplitude of the signal with frequency twice the selected component's frequency corresponds to the selected frequency component.

In some embodiments, a pulsed system (time domain multiplexed) system with tuning agility by processor control is possible. However, the filters should be designed and the measurements timed such that appropriate settling times are taken into account. There is a trade-off between filter Q and settling time—they are inversely related. The application of this tunable technology can form the basis of a bedside diagnostic suite for future clinical treatments.

Figure 8:
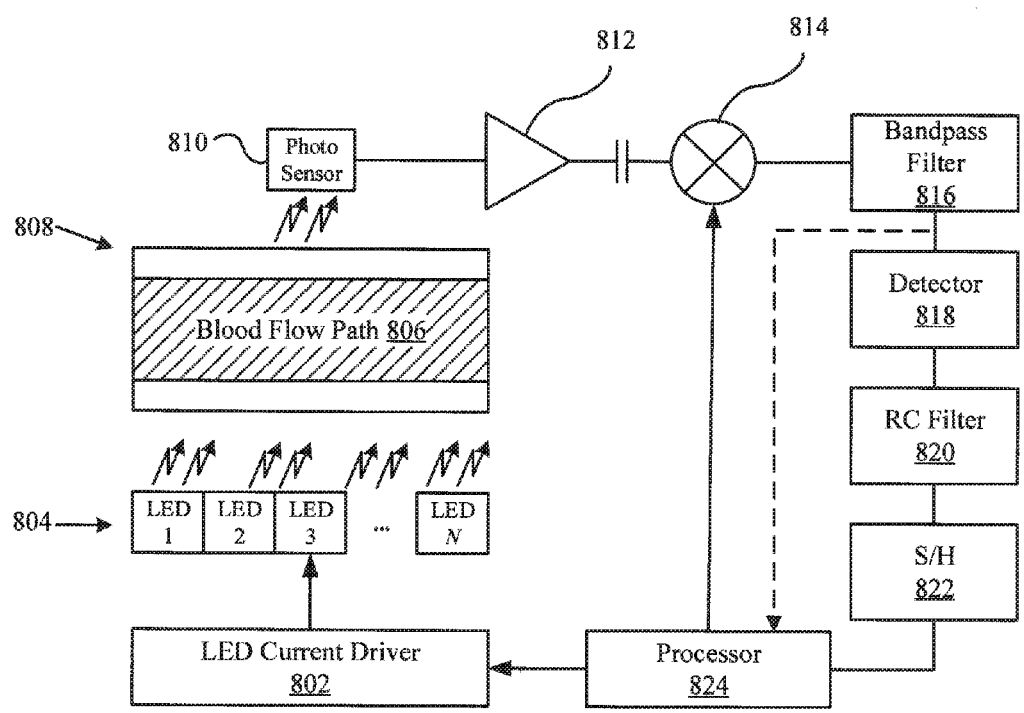
FIG. 8 illustrates an exemplary system for measuring blood constituents according to some embodiments of the disclosure.

FIG. 8 illustrates a system that may take advantage of a synchronous optical receiver according to some embodiments of the disclosure. The system in FIG. 8 is used to measure blood constituents utilizing some embodiments of the disclosure. An LED current driver 802 produces multiple currents to drive an LED array 804. The LED array 804 contains LED1 to LEDN. Each LED in the LED array 804 operates at a different wavelength, and the LED current driver 802 is configured to modulate the current provided to each LED. Each modulated current behaves in a sinusoidal manner, with frequency much lower than the frequencies of the LEDs in the LED array 802. The modulated currents all have different frequencies from one another and do not exhibit a harmonic relationship with each other.

FIG. 8 shows that processor 824 controls the LED current driver 802, so in some embodiments, the processor 824 may determine which modulation frequencies the LED current driver 802 should provide to each LED in the LED array 804. Light from the LED array 804 is incident on a blood chamber 808 and then through a blood flow path 806 and then to a photodetector or photosensor 810 which may be a photodiode. The photosensor 810 collects and integrates all light input (including ambient light) and generates a current. The current is then amplified and converted to a voltage signal by Trans-Z amplifier 812. A DC blocking capacitor is used to filter out the ambient light and introduce the amplified signal to the multiplier 814.

The composite signal received at the multiplier 814 contains M(t) frequency components from the multiple LEDs in the LED array 804. In some embodiments, the processor 824 provides to the multiplier 814, a frequency that is equal to the M(t) modulating frequency of LED2. The multiplier 814 then generates new frequency components including a frequency component that is two times the M(t) modulating frequency of LED2. Bandpass filter 816 is designed with a center frequency at two times the modulating frequency of LED2, so the bandpass filter 816 selects this frequency and attenuates all other frequencies of the LEDs. The detector 818, RC filter 820, and S/H 822 all operate as in FIG. 5 to extract a value corresponding to the amplitude of the signal with twice the modulating frequency of LED2. This value is provided to processor 824, and processor 824 may communicate this value to other systems and/or interpret the concentration of the constituent sensed by LED2 by using the amplitude of the signal driving LED2 and the value received by the S/H 822.

In the previous system, LED2 was used as an example, but any of the modulation frequencies M(t) of the LEDs in the LED array 804 may have been tuned to. Additionally, using the bandpass filter 816 to select twice the modulating frequency is also used as an example. As previously mentioned, there are at least three ways of detection—using twice the modulating frequency, detecting a DC signal, and detecting an offset frequency. Therefore, the processor 824 may provide a frequency different from one of the modulating frequencies of an LED in the LED array 804, and bandpass filter 816 may be substituted for a lowpass filter depending on the method of sensing.

In addition, the dashed line linking the bandpass filter 816 and the processor 824 is an optional path to determine the phase difference between the signal from the bandpass filter 816 and one of the M(t) modulation frequency current signals provided to the LED array 804 by LED current driver 802. The dotted line signal may drive a phase locked loop or algorithm or system included in the processor 824 or an external equivalent device inserted in the dotted line. In some cases, a frequency divider is included in the processor 824 to correct for the frequency adjustments of the multiplier. For example, if the signal from the bandpass filter 816 has a frequency that is twice that of the modulated frequency current signal, then the processor 824 divides this frequency by 2 for the phase comparison.

In FIG. 3, example frequency tags were provided to measure the concentration of different blood constituents. f1 was selected to measure oxygenated hemoglobin ($HbO_2$), f2 to measure sodium, f3 to measure platelets, f4 to measure isosbestic hemoglobin, f5 to measure carboxi-hemoglobin, and f6 to measure water. In a blood constituent system with an optical receiver using f1 to f6 to measure the blood constituents according to some embodiments of the disclosure, the signal amplitudes of each selected frequency is converted to a concentration of the constituent. For example, using the system of FIG. 8, LED1 emits light modulated at f1, LED2 emits light modulated at f2 . . . , and LED6 emits light modulated at f6. Processor 824 selects consecutively f1, f2 . . . f6, and obtains values V1, V2 . . . V6 from S/H 822 for each of the selected frequency signals. V1, V2 . . . V6 represent values dependent on a concentration of the measured constituent. For example, the value of V1 is dependent on a concentration of $HbO_2$ ($[HbO_2]$).

For measurements, information corresponding to ratios is desired, and the values obtained from S/H 822 may be used directly. For example, the natural log (ln) of V1 divided by ln(V4) corresponds to $[HbO_2]/[Hb]$ which may be used to determine oxygen saturation of blood. ln(V4) divided by ln(V6) corresponds to $[Hb]/[H_2O]$ which may be used to determine hematocrit. ln(V3) divided by ln(V6) corresponds to $[Platelets]/[H_2O]$ which may be used to determine blood platelet content. The log ratios are mapped to a calibrated functional relationship between the value obtained from a ratio and the concentration of the information desired.

The measurement system in FIG. 8 should be calibrated for each item being measured. For example, when calibrating to measure oxygen saturation of blood, a blood sample is used to obtain $V1_{cal,x}$ and $V4_{cal,x}$, where "cal" denotes calibration, and "x" denotes the measurement number. That is, in a first measurement, the blood sample will provide $V1_{cal,1}$ and $V4_{cal,1}$, and in a second measurement, the blood sample will provide $V1_{cal,2}$ and $V4_{cal,2}$. Calibration process involves first measuring $V1_{cal,1}$ and $V4_{cal,1}$ and then using a Co-oximeter to measure the oxygen saturation of blood. Afterwards, introducing nitrogen into the blood sample to reduce the oxygen saturation of the blood sample, making a second measurement to obtain $V1_{cal,2}$ and $V4_{cal,2}$, and then using the Co-oximeter to measure the oxygen saturation of blood. Then the process further involves reducing the concentration of oxygen in the blood sample and repeating the measurements. After obtaining enough datapoints comprising $V1_{cal,x}$, $V4_{cal,x}$, and measured oxygen concentrations from the Co-oximeter, statistical regression for oxygen concentration may be performed on the ratio of $\ln(V1_{cal,x})/\ln(V4_{cal,x})$ to obtain a functional relationship between oxygen and the ratio $\ln(V1_{cal,x})/\ln(V4_{cal,x})$. Once this functional or graphical relationship is obtained, any measurements made from the ratio ln(V1) divided by ln(V4) may be mapped to an oxygen concentration derived in this relationship.

The modulation frequency and constituents in FIG. 3 are combined here with the embodiment provided in FIG. 8 as an example. Other constituents may be sensed with other types and numbers of emitters and photodetectors.

Figure 9:
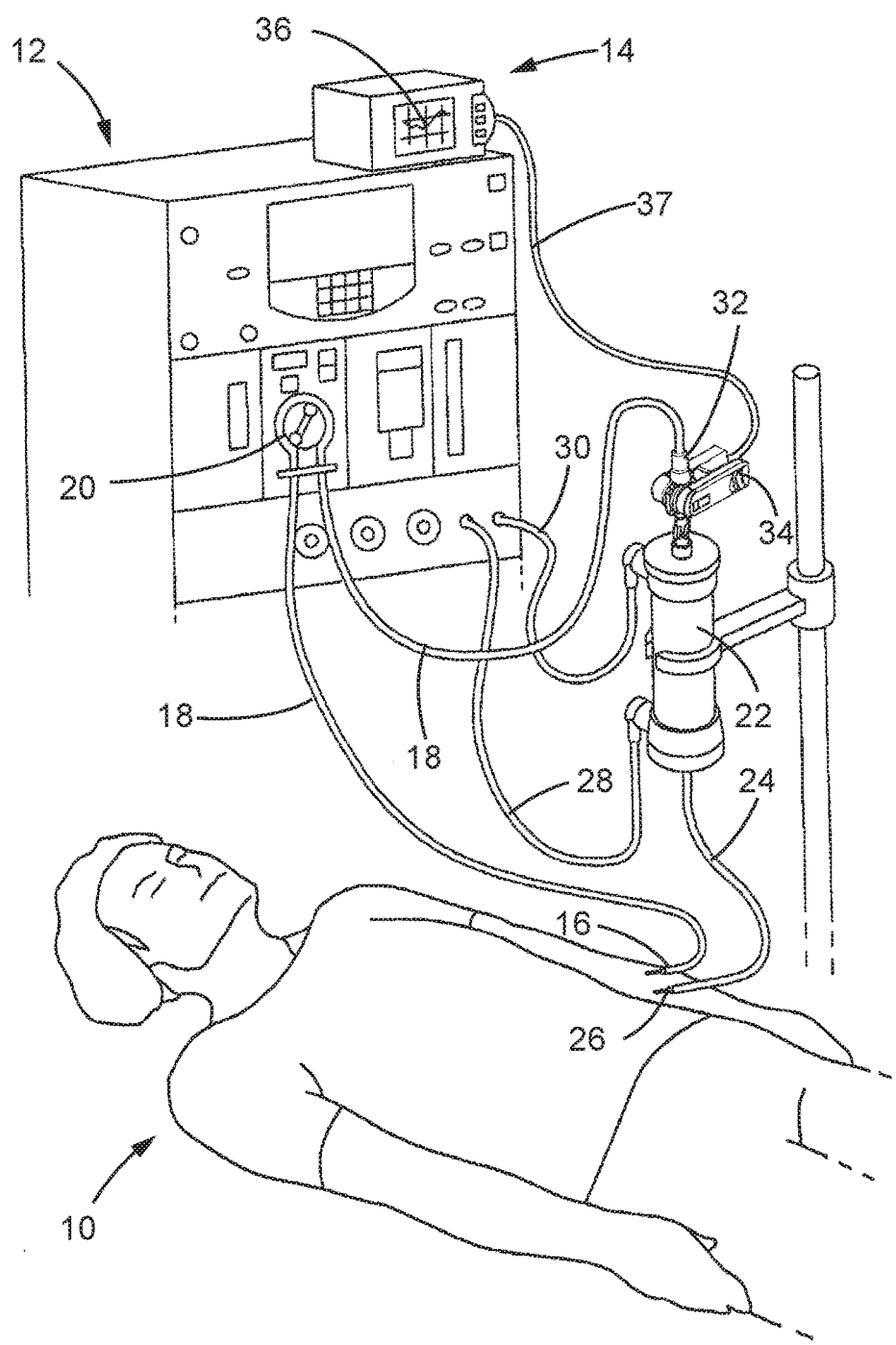
FIG. 9 illustrates an exemplary blood monitoring system as part of a dialysis treatment system.

FIG. 9 illustrates an exemplary environment of a blood monitoring system incorporating an embodiment of the tunable optical receiver for a dialysis treatment. A patient 10 in FIG. 9 is attached to the dialysis treatment system 12 via a blood extraction needle 16 and blood injection needle 26. During a dialysis treatment with the dialysis treatment system 12, blood is extracted from the patient 10 via blood extraction needle 16, passed through the blood pump 20, the blood chamber 32 and dialyzer blood filter 22 using tubes 18, and then returned back to the patient 10 via tube 24 and blood injection needle 26. The dialyzer 22 filters the blood by fluid exchange with dialysis solution from fresh dialysis tube 28 and deposits filtered waste out to used dialysis tube 30.

A blood monitoring system including a display 14, cable, and an optical transmitter and receiver assembly 34 is used with a dialysis treatment system 12 for monitoring certain blood characteristics relevant to the dialysis process. The optical transmitter and receiver assembly 34 mates to a blood chamber 32 in a blood flow path provided by the tubes 18. Optical transmitter and receiver assembly 34 includes light emitters and photodetectors that are positioned on opposite sides of the blood chamber 32 when the optical transmitter and receiver assembly is mated to the blood chamber. Light passing through the blood chamber from the light emitters in the optical transmitter and receiver assembly 34 is absorbed by the blood undergoing dialysis. Photodetectors in the optical transmitter and receiver assembly 34 detect the absorption and circuitry process absorption signals from the photodetectors to provide information at the display 14 meaningful to the clinician responsible for the dialysis process. The circuitry that processes the absorption signals may use embodiments of tunable optical receivers in the disclosure.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions.

Software implementations of aspects of the system described herein may include executable code that is stored in a computer readable medium and executed by one or more processors. The computer readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system for determining information on one or more constituents in a medium, the system comprising:

N light emitters $L_1 \ldots L_N$, wherein each light emitter $L_x$ is configured to provide an amplitude modulated (AM) light at modulation frequency $f_x$ into a flow path of the medium from one side of a containment vessel for the medium, wherein each light emitter $L_x$ uses a different modulation frequency $f_x$, wherein N is an integer greater than 1, and x is an integer greater than or equal to 1 and less than or equal to N, and wherein within the modulation frequencies $f_1 \ldots f_N$, no two modulation frequencies are harmonically related;

a photodetector configured to receive the AM light from each light emitter after it passes through the flow path of the medium, and convert the AM light to an electrical signal characterized by a summation of frequency components from each modulation frequency $f_x$;

a blocking capacitor configured to remove a DC offset from the electrical signal;

a multiplier configured to generate a mixed output signal by multiplying the electrical signal without DC offset and a matching signal; and one or more measuring circuits configured to provide information about a concentration of one or more constituents in the medium by processing the mixed output signal to determine log ratios of a pair of amplitudes of $f_y$ and $f_z$ frequency components in the electrical signal, wherein y and z are integers greater than or equal to 1 and less than or equal to N, and y is not equal to z.

2. The system according to claim 1, wherein the medium is blood moving through a blood chamber.

3. The system according to claim 2, wherein the blood chamber is part of a device for monitoring blood undergoing dialysis.

4. The system according to claim 1, wherein:

the matching signal has a frequency equal to one of the modulation frequencies $f_1 \ldots f_N$;

the one or more measuring circuits is one measuring circuit, the measuring circuit comprising a bandpass filter and a processor;

the processor is configured to select the frequency of the matching signal, and the bandpass filter is configured to extract a filtered signal from the mixed output signal, the filtered signal having a frequency equal to twice the matching signal's frequency; and the measuring circuit determines values $V_y$ from the filtered signal when the matching frequency is $f_y$ and $V_z$ from the filtered signal when the matching frequency is $f_z$, and $V_y$ and $V_z$ are related to the amplitudes of the $f_y$ and $f_z$ frequency components in the electrical signal, where the log ratios of $V_y$ and $V_z$ includes the information about the concentration of the constituents.

5. The system according to claim 1, wherein:

the matching signal has a frequency equal to one of the modulation frequencies $f_1 \ldots f_N$;

the one or more measuring circuits is one measuring circuit, the measuring circuit comprising a lowpass filter and a processor;

the processor is configured to select the frequency of the matching signal, and the lowpass filter is configured to extract a filtered signal from the mixed output signal, the filtered signal being a DC signal; and the measuring circuit determines values $V_y$ from the filtered signal when the matching frequency is $f_y$ and $V_z$ from the filtered signal when the matching frequency is $f_z$, and $V_y$ and $V_z$ are related to the amplitudes of the $f_y$ and $f_z$ frequency components in the electrical signal, where the log ratios of $V_y$ and $V_z$ includes the information about the concentration of the constituents.

6. The system according to claim 1, wherein:

the matching signal has a frequency equal to one of the modulation frequencies $f_1 \ldots f_N$ plus an offset frequency;

the one or more measuring circuits is one measuring circuit, the measuring circuit comprising a bandpass filter and a processor;

the processor is configured to select the frequency of the matching signal, and the bandpass filter is configured to extract a filtered signal from the mixed output signal, the filtered signal having a frequency equal to the offset frequency; and the measuring circuit determines values $V_y$ from the filtered signal when the matching frequency is $f_y$ plus the offset frequency and $V_z$ from the filtered signal when the matching frequency is $f_z$ plus the offset frequency, and $V_y$ and $V_z$ are related to the amplitudes of the $f_y$ and $f_z$ frequency components in the electrical signal, where the log ratios of $V_y$ and $V_z$ includes the information about the concentration of the constituents.

7. A method for determining information on one or more constituents in a medium, the method comprising:
varying, by a driving circuit, current provided to N light emitters $L_1 \ldots L_N$ in a sinusoidal manner so that each light emitter $L_x$ provides an amplitude modulated (AM) light at modulation frequency $f_x$ into a flow path of the medium from one side of a containment vessel for the medium, wherein each light emitter $L_x$ uses a different modulation frequency $f_x$, wherein N is an integer greater than 1, and x is an integer greater than or equal to 1 and less than or equal to N, and wherein within the modulation frequencies $f_1 \ldots f_N$, no two modulation frequencies are harmonically related;
receiving, by a photodetector, the AM light from each light emitter after it passes through the flow path of the medium and converting the AM light to an electrical signal characterized by a summation of frequency components from each modulation frequency $f_x$;
removing a DC offset from the electrical signal;
generating, by a multiplier, two mixed output signals by multiplying the electrical signal without DC offset and two matching signals; and
extracting, by a measuring circuit, log ratios of the amplitudes of $f_y$ and $f_z$ frequency components in the electrical signal by processing the two mixed output signals to determine information about a concentration of one or more constituents in the medium, wherein y and z are integers greater than or equal to 1 and less than or equal to N, and y is not equal to z.

8. The method according to claim 7, wherein the medium is blood moving through a blood chamber.

9. The method according to claim 8, wherein the blood chamber is part of a device for monitoring blood undergoing dialysis.

10. The method according to claim 7,
wherein the two matching signals have frequencies $f_y$ and $f_z$, and wherein the method further comprises:
extracting, by a bandpass filter, two corresponding filtered signals from the two mixed output signals, the two filtered signals having frequencies equal to $2 \times f_y$ and $2 \times f_z$; and
determining, by the measuring circuit, values $V_y$ from the filtered signals when the matching frequency is $f_y$ and $V_z$ from the filtered signals when the matching frequency is $f_z$, and $V_y$ and $V_z$ are related to the amplitudes of the $f_y$ and $f_z$ frequency components in the electrical signal, where the log ratios of $V_y$ and $V_z$ includes the information about the concentration of the constituents.

11. The method according to claim 7,
wherein the two matching signals have frequencies $f_y$ and $f_z$, and wherein the method further comprises:
extracting, by a lowpass filter, two corresponding filtered signals from the two mixed output signals, the two filtered signals being DC signals; and
determining, by the measuring circuit, values $V_y$ from the filtered signals when the matching frequency is $f_y$ and $V_z$ from the filtered signals when the matching frequency is $f_z$, and $V_y$ and $V_z$ are related to the amplitudes of the $f_y$ and $f_z$ frequency components in the electrical signal, where the log ratios of $V_y$ and $V_z$ includes the information about the concentration of the constituents.

12. The method according to claim 7,
wherein the two matching signals have frequencies $f_y$ plus an offset frequency and $f_z$ plus the offset frequency, and wherein the method further comprises:
extracting, by a bandpass filter, two corresponding filtered signals from the two mixed output signal, the two filtered signals having frequencies equal to the offset frequency; and
determining, by the measuring circuit, values $V_y$ from the filtered signals when the matching frequency is $f_y$ plus the offset frequency and $V_z$ from the filtered signals when the matching frequency is $f_z$ plus the offset frequency, and $V_y$ and $V_z$ are related to the amplitudes of the $f_y$ and $f_z$ frequency components in the electrical signal, where the log ratios of $V_y$ and $V_z$ includes the information about the concentration of the constituents.

13. A non-transient computer readable medium containing program instructions for determining information on one or more constituents in a medium, such that when the instructions are executed by a processor coupled to N light emitters $L_1 \ldots L_N$ and a photodetector, the processor performs the method of:
varying driving current provided to the N light emitters in a sinusoidal manner so that each light emitter $L_x$ provides an amplitude modulated (AM) light at modulation frequency $f_x$ into a flow path of the medium from one side of a containment vessel for the medium, wherein each light emitter $L_x$ uses a different modulation frequency $f_x$, wherein N is an integer greater than 1, and x is an integer greater than or equal to 1 and less than or equal to N, and wherein within the modulation frequencies $f_1 \ldots f_N$, no two modulation frequencies are harmonically related;
receiving an electrical signal without DC offset from a blocking capacitor coupled to the photodetector, wherein the electrical signal without DC offset is generated from an electrical signal representing the AM light from each light emitter received at the photodetector after the AM light passes through the flow path of the medium;
providing two matching signals with frequencies $f_y$ and $f_z$ to a multiplier, so that the multiplier generates two mixed output signals by multiplying the electrical signal without DC offset and the two matching signals; and
extracting log ratios of amplitudes of $f_y$ and $f_z$ frequency components in the electrical signal by processing the two mixed output signals to determine information about a concentration of one or more constituents in the medium, wherein y and z are integers greater than or equal to 1 and less than or equal to N, and y is not equal to z;
wherein the electrical signal is characterized by a summation of frequency components from each modulation frequency $f_x$.

14. The non-transient computer readable medium according to claim 13, wherein the processor further performs the method of:
extracting log ratios of values $V_y$ and $V_z$ to determine the information about the concentration of the constituents, wherein $V_y$ is determined from a filtered signal in one mixed output signal with frequency $2 \times f_y$ when the matching frequency is $f_y$ and $V_z$ is determined from a filtered signal in the other mixed output signal with frequency $2 \times f_z$ when the matching frequency is $f_z$, and $V_y$ and $V_z$ are related to the amplitudes of the $f_y$ and $f_z$ frequency components in the electrical signal.

15. A system for determining information on one or more constituents in a medium, the system comprising:

N light emitters $L_1 \ldots L_N$, wherein each light emitter $L_x$ is configured to provide an amplitude modulated (AM) light at modulation frequency $f_x$ into a flow path of the medium from one side of a containment vessel for the medium, wherein each light emitter $L_x$ uses a different modulation frequency $f_x$, and wherein N is an integer greater than 1, and x is an integer greater than or equal to 1 and less than or equal to N;

a photodetector configured to receive the AM light from each light emitter after it passes through the flow path of the medium, and convert the AM light to an electrical signal characterized by a summation of frequency components from each modulation frequency $f_x$; and one or more measuring circuits configured to:

provide information about a concentration of one or more constituents in the medium determined from log ratios of a pair of amplitudes of $f_y$ and $f_z$ frequency components in the electrical signal, wherein y and z are integers greater than or equal to 1 and less than or equal to N, and y is not equal to z, provide a phase difference between a phase of an $f_x$ frequency component of the electrical signal and a phase of a current driving the $L_x$ emitter, and determine a change in the phase difference, wherein the change in the phase difference provides information about a change in the composition of the medium.

16. A method for determining information on one or more constituents in a medium, the method comprising:

varying, by a driving circuit, current provided to N light emitters $L_1 \ldots LN$ in a sinusoidal manner so that each light emitter $L_x$ provides an amplitude modulated (AM) light at modulation frequency $f_x$ into a flow path of the medium from one side of a containment vessel for the medium, wherein each light emitter $L_x$ uses a different modulation frequency $f_x$, and wherein N is an integer greater than 1, and x is an integer greater than or equal to 1 and less than or equal to N;

receiving, by a photodetector, the AM light from each light emitter after it passes through the flow path of the medium and converting the AM light to an electrical signal characterized by a summation of frequency components from each modulation frequency $f_x$;

extracting, by a measuring circuit, log ratios of the amplitudes of $f_y$ and $f_z$ frequency components in the electrical signal to determine information about a concentration of one or more constituents in the medium, wherein y and z are integers greater than or equal to 1 and less than or equal to N, and y is not equal to z;

determining, by the measuring circuit, a phase difference between a phase of an $f_x$ frequency component of the electrical signal and a phase of a current driving the $L_x$ emitter; and determining, by the measuring circuit, a change in the phase difference, wherein the change in the phase difference provides information about a change in the composition of the medium.

\* \* \* \* \*